US009408547B2

(12) United States Patent
Zhou et al.

(10) Patent No.: US 9,408,547 B2
(45) Date of Patent: Aug. 9, 2016

(54) ECG ELECTRODE CONNECTOR

(71) Applicant: Covidien LP, Mansfield, MA (US)

(72) Inventors: David Zhou, Shenzhen (CN); Peter Yu, Shenzhen (CN)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 14/160,798

(22) Filed: Jan. 22, 2014

(65) Prior Publication Data

US 2014/0309514 A1    Oct. 16, 2014

Related U.S. Application Data

(63) Continuation of application No. PCT/CN2011/077506, filed on Jul. 22, 2011.

(51) Int. Cl.
*H01R 13/187* (2006.01)
*A61B 5/0416* (2006.01)
*A61B 6/03* (2006.01)
*A61B 5/055* (2006.01)

(52) U.S. Cl.
CPC ............... *A61B 5/0416* (2013.01); *A61B 5/055* (2013.01); *A61B 6/032* (2013.01); *A61B 2560/0406* (2013.01); *A61B 2562/227* (2013.01)

(58) Field of Classification Search
CPC ........... H01R 2201/12; H01R 13/5224; H01R 13/187
USPC .................................................. 439/668, 729
See application file for complete search history.

(56) References Cited

U.S. PATENT DOCUMENTS

| 3,606,881 | A | 9/1971 | Woodson |
| 3,752,151 | A | 8/1973 | Robichaud |
| 3,805,769 | A | 4/1974 | Sessions |
| 3,828,766 | A | 8/1974 | Krasnow |
| 3,829,826 | A | 8/1974 | Brown et al. |
| 3,842,394 | A | 10/1974 | Bolduc |
| 3,868,946 | A | 3/1975 | Hurley |
| 3,888,240 | A | 6/1975 | Reinhold, Jr. et al. |
| 3,895,635 | A | 7/1975 | Justus et al. |
| 3,901,218 | A | 8/1975 | Buchalter |

(Continued)

FOREIGN PATENT DOCUMENTS

| CN | 101491437 A | 7/2009 |
| CN | 101491438 A | 7/2009 |

(Continued)

OTHER PUBLICATIONS

Response filed on Feb. 6, 2015; for Office Action dated Sep. 10, 2014; for U.S. Appl. No. 14/324,380; 8 pages.

(Continued)

*Primary Examiner* — Truc Nguyen

(57) ABSTRACT

Disclosed is an ECG electrode lead wire connector which provides improved electrical and mechanical coupling of the ECG electrode press stud to the lead wire and is suitable for use during imaging procedures such as, without limitation, CT scans or MRI. The connector assembly includes a housing having. An engagement member is pivotably disposed within the housing to retain the connector on an ECG electrode fixed to a patient's body, an arcuate stiffener is deposed between the engagement member and a pivot member and a radiolucent resilient member configured to bias the engagement member.

9 Claims, 8 Drawing Sheets

(56) References Cited

U.S. PATENT DOCUMENTS

| | | | |
|---|---|---|---|
| 3,997,225 | A | 12/1976 | Horwinski |
| 3,998,213 | A | 12/1976 | Price |
| 4,027,664 | A | 6/1977 | Heavner, Jr. et al. |
| 4,034,854 | A | 7/1977 | Bevilacqua |
| 4,077,397 | A | 3/1978 | Ellis et al. |
| 4,112,941 | A | 9/1978 | Larimore |
| 4,166,465 | A | 9/1979 | Esty et al. |
| 4,220,390 | A | 9/1980 | Cobaugh et al. |
| 4,303,293 | A | 12/1981 | Grunwald |
| D263,167 | S | 2/1982 | Stone |
| 4,353,372 | A | 10/1982 | Ayer |
| 4,365,634 | A | 12/1982 | Bare et al. |
| 4,498,480 | A | 2/1985 | Mortensen |
| 4,674,817 | A | 6/1987 | Olms |
| 4,729,377 | A | 3/1988 | Granek et al. |
| 4,763,660 | A | 8/1988 | Kroll et al. |
| 4,781,200 | A | 11/1988 | Baker |
| 4,785,822 | A | 11/1988 | Wallace |
| 4,815,964 | A | 3/1989 | Cohen et al. |
| 4,842,557 | A | 6/1989 | Muz |
| 4,850,356 | A | 7/1989 | Heath |
| 4,909,260 | A | 3/1990 | Salem et al. |
| 4,947,846 | A | 8/1990 | Kitagawa et al. |
| 4,957,109 | A | 9/1990 | Groeger et al. |
| 4,974,594 | A | 12/1990 | Berlin |
| 5,080,604 | A | 1/1992 | Rider et al. |
| 5,083,238 | A | 1/1992 | Bousman |
| 5,083,933 | A | 1/1992 | Colleran et al. |
| 5,104,253 | A | 4/1992 | Zielinski et al. |
| 5,104,334 | A | 4/1992 | Honma et al. |
| 5,131,854 | A | 7/1992 | Jose et al. |
| 5,137,466 | A | 8/1992 | Endo et al. |
| 5,154,646 | A | 10/1992 | Shoup |
| 5,158,469 | A | 10/1992 | Martin |
| 5,160,276 | A | 11/1992 | Marsh et al. |
| 5,173,059 | A | 12/1992 | Sato et al. |
| 5,176,343 | A | 1/1993 | Cheney et al. |
| 5,178,556 | A | 1/1993 | Chen |
| 5,180,312 | A | 1/1993 | Martin |
| 5,190,467 | A | 3/1993 | Ohta |
| 5,192,226 | A | 3/1993 | Wang |
| 5,197,901 | A | 3/1993 | Hashiguchi |
| 5,199,897 | A | 4/1993 | Hashiguchi |
| 5,201,669 | A | 4/1993 | Lin |
| 5,203,715 | A | 4/1993 | Yamamoto |
| 5,203,719 | A | 4/1993 | Kozono |
| 5,207,594 | A | 5/1993 | Olson |
| 5,224,479 | A | 7/1993 | Sekine |
| 5,232,383 | A | 8/1993 | Barnick |
| 5,234,357 | A | 8/1993 | Yamaguchi |
| 5,243,510 | A | 9/1993 | Cheney |
| 5,263,481 | A | 11/1993 | Axelgaard |
| 5,276,443 | A | 1/1994 | Gates et al. |
| 5,278,759 | A | 1/1994 | Berra et al. |
| 5,279,308 | A | 1/1994 | DiSabito et al. |
| 5,293,013 | A | 3/1994 | Takahashi |
| 5,320,621 | A | 6/1994 | Gordon et al. |
| 5,326,272 | A | 7/1994 | Harhen et al. |
| 5,332,330 | A | 7/1994 | Kaneko |
| 5,338,219 | A | 8/1994 | Hiramoto |
| 5,341,806 | A | 8/1994 | Gadsby et al. |
| 5,341,812 | A | 8/1994 | Allaire et al. |
| 5,353,793 | A | 10/1994 | Bornn |
| 5,354,216 | A | 10/1994 | Cruise et al. |
| 5,362,249 | A | 11/1994 | Carter |
| 5,370,116 | A | 12/1994 | Rollman et al. |
| 5,370,550 | A | 12/1994 | Alwine et al. |
| 5,376,016 | A | 12/1994 | Inaba et al. |
| 5,378,168 | A | 1/1995 | Sumida |
| 5,380,223 | A | 1/1995 | Marsh et al. |
| 5,382,176 | A | 1/1995 | Norden |
| 5,383,794 | A | 1/1995 | Davis et al. |
| 5,387,116 | A | 2/1995 | Wang |
| 5,387,127 | A | 2/1995 | Wang |
| 5,399,045 | A | 3/1995 | Yoneda et al. |
| 5,405,269 | A | 4/1995 | Stupecky |
| 5,415,164 | A | 5/1995 | Faupel et al. |
| 5,429,526 | A | 7/1995 | Ann |
| 5,431,166 | A | 7/1995 | Macur |
| 5,454,739 | A | 10/1995 | Strand |
| 5,462,448 | A | 10/1995 | Kida et al. |
| 5,484,739 | A | 1/1996 | Lee et al. |
| 5,486,117 | A | 1/1996 | Chang |
| 5,507,290 | A | 4/1996 | Kelly et al. |
| 5,507,665 | A | 4/1996 | Oda |
| 5,507,668 | A | 4/1996 | Lambrinos et al. |
| 5,509,822 | A | 4/1996 | Negus et al. |
| 5,511,553 | A | 4/1996 | Segalowitz |
| 5,546,950 | A | 8/1996 | Schoeckert et al. |
| 5,558,535 | A | 9/1996 | Saka et al. |
| 5,564,939 | A | 10/1996 | Maitani et al. |
| 5,582,180 | A | 12/1996 | Manset et al. |
| 5,584,719 | A | 12/1996 | Tsuji et al. |
| D377,219 | S | 1/1997 | Strand et al. |
| 5,599,199 | A | 2/1997 | Wright |
| 5,603,632 | A | 2/1997 | Johannes et al. |
| 5,611,708 | A | 3/1997 | Mizunuma et al. |
| 5,613,870 | A | 3/1997 | Traver, Jr. |
| 5,615,674 | A | 4/1997 | Maurer |
| 5,622,168 | A | 4/1997 | Keusch et al. |
| 5,624,271 | A | 4/1997 | Childs et al. |
| 5,624,281 | A | 4/1997 | Christensson |
| 5,626,135 | A | 5/1997 | Sanfilippo |
| 5,632,274 | A | 5/1997 | Quedens et al. |
| 5,651,689 | A | 7/1997 | Plyler et al. |
| 5,653,606 | A | 8/1997 | Chrysostomou |
| 5,674,088 | A | 10/1997 | Roche et al. |
| 5,676,694 | A | 10/1997 | Boser et al. |
| 5,679,022 | A | 10/1997 | Cappa |
| 5,679,029 | A | 10/1997 | Saunier et al. |
| 5,685,303 | A | 11/1997 | Rollman et al. |
| 5,695,355 | A | 12/1997 | Hasenfratz et al. |
| 5,702,265 | A | 12/1997 | Yamaguchi |
| 5,704,351 | A | 1/1998 | Mortara et al. |
| 5,711,684 | A | 1/1998 | Inoue et al. |
| 5,718,596 | A | 2/1998 | Inaba et al. |
| 5,724,025 | A | 3/1998 | Tavori |
| 5,724,984 | A | 3/1998 | Arnold et al. |
| 5,725,525 | A | 3/1998 | Kordis |
| 5,741,155 | A | 4/1998 | Herman |
| 5,749,746 | A | 5/1998 | Tan et al. |
| 5,769,650 | A | 6/1998 | Aoyama et al. |
| 5,772,591 | A | 6/1998 | Cram |
| 5,775,953 | A | 7/1998 | Yamanashi et al. |
| 5,782,647 | A | 7/1998 | Okura et al. |
| 5,782,761 | A | 7/1998 | Gusakov |
| 5,782,892 | A | 7/1998 | Castle et al. |
| 5,788,527 | A | 8/1998 | Sanders et al. |
| 5,791,918 | A | 8/1998 | Pierce |
| 5,797,854 | A | 8/1998 | Hedgecock |
| 5,806,152 | A | 9/1998 | Saitou et al. |
| 5,813,404 | A | 9/1998 | Devlin et al. |
| 5,813,979 | A | 9/1998 | Wolfer |
| 5,827,086 | A | 10/1998 | Fukuda |
| 5,830,000 | A | 11/1998 | Shifflett et al. |
| 5,836,783 | A | 11/1998 | Morisawa et al. |
| 5,843,141 | A | 12/1998 | Bischoff et al. |
| 5,848,456 | A | 12/1998 | Sjoqvist |
| 5,865,740 | A | 2/1999 | Kelly et al. |
| 5,865,741 | A | 2/1999 | Kelly et al. |
| 5,871,451 | A | 2/1999 | Unger et al. |
| 5,873,747 | A | 2/1999 | Tsuji |
| 5,876,232 | A | 3/1999 | Matsushita et al. |
| 5,895,284 | A | 4/1999 | Kocher et al. |
| 5,895,298 | A | 4/1999 | Faupel |
| 5,904,579 | A | 5/1999 | McLean et al. |
| 5,913,834 | A | 6/1999 | Francais |
| 5,916,159 | A | 6/1999 | Kelly et al. |
| 5,931,689 | A | 8/1999 | Patel |
| 5,931,861 | A | 8/1999 | Werner et al. |
| 5,934,926 | A | 8/1999 | Gabrisko, Jr. et al. |
| 5,937,950 | A | 8/1999 | Adams et al. |
| 5,938,470 | A | 8/1999 | Kashiyama |
| 5,938,597 | A | 8/1999 | Starbucker |

(56) References Cited

U.S. PATENT DOCUMENTS

| | | |
|---|---|---|
| 5,941,725 A | 8/1999 | Brennan et al. |
| 5,944,562 A * | 8/1999 | Christensson ....... A61B 5/0416 439/261 |
| 5,951,316 A | 9/1999 | Kawano et al. |
| 5,964,624 A | 10/1999 | Pernelle |
| 5,968,087 A | 10/1999 | Hess et al. |
| 5,971,790 A | 10/1999 | Rohde |
| 5,971,799 A | 10/1999 | Swade |
| 5,980,332 A | 11/1999 | Tsuji et al. |
| 5,984,717 A | 11/1999 | Lee |
| 5,997,334 A | 12/1999 | Goto |
| 6,006,125 A | 12/1999 | Kelly et al. |
| 6,027,359 A | 2/2000 | Aoki et al. |
| 6,032,063 A | 2/2000 | Hoar et al. |
| 6,032,064 A | 2/2000 | Devlin et al. |
| 6,038,479 A | 3/2000 | Werner et al. |
| 6,038,481 A | 3/2000 | Werner et al. |
| 6,050,838 A | 4/2000 | Norizuki et al. |
| 6,055,448 A | 4/2000 | Anderson et al. |
| 6,062,902 A | 5/2000 | Buckles et al. |
| 6,066,093 A | 5/2000 | Kelly et al. |
| 6,074,234 A | 6/2000 | Hasegawa |
| 6,098,127 A | 8/2000 | Kwang |
| 6,109,948 A | 8/2000 | Kuo |
| 6,115,623 A | 9/2000 | McFee |
| 6,116,940 A | 9/2000 | Bertens et al. |
| 6,122,536 A | 9/2000 | Sun et al. |
| 6,122,544 A | 9/2000 | Organ |
| 6,129,666 A | 10/2000 | DeLuca et al. |
| 6,132,233 A | 10/2000 | Fukuda |
| 6,139,350 A | 10/2000 | Mathesius |
| 6,139,360 A | 10/2000 | Hayashi |
| 6,152,778 A | 11/2000 | Dalton |
| 6,155,864 A | 12/2000 | Yoshiura |
| 6,157,851 A | 12/2000 | Kelly et al. |
| 6,165,017 A | 12/2000 | Kuo |
| 6,168,453 B1 | 1/2001 | Kuo |
| 6,171,139 B1 | 1/2001 | Sato et al. |
| 6,190,385 B1 | 2/2001 | Tom et al. |
| 6,203,354 B1 | 3/2001 | Kuwahara |
| 6,219,568 B1 | 4/2001 | Kelly et al. |
| 6,219,569 B1 | 4/2001 | Kelly et al. |
| 6,223,088 B1 | 4/2001 | Scharnberg et al. |
| 6,232,366 B1 | 5/2001 | Wang et al. |
| 6,234,827 B1 | 5/2001 | Nishio et al. |
| 6,236,874 B1 | 5/2001 | Devlin et al. |
| 6,240,323 B1 | 5/2001 | Calenzo, Sr. et al. |
| 6,247,963 B1 | 6/2001 | Rattner |
| 6,250,955 B1 | 6/2001 | Archuleta |
| 6,254,425 B1 | 7/2001 | Shchervinsky |
| 6,257,914 B1 | 7/2001 | Comerci et al. |
| 6,257,925 B1 | 7/2001 | Jones |
| 6,280,209 B1 | 8/2001 | Bassler et al. |
| 6,280,227 B1 | 8/2001 | Terada et al. |
| 6,280,243 B1 | 8/2001 | Liu et al. |
| 6,283,789 B1 | 9/2001 | Tsai |
| 6,290,530 B1 | 9/2001 | Chang |
| 6,298,255 B1 | 10/2001 | Cordero et al. |
| 6,304,783 B1 | 10/2001 | Lyster et al. |
| 6,312,297 B1 | 11/2001 | Lorkowski |
| 6,324,432 B1 | 11/2001 | Rigaux et al. |
| D452,318 S | 12/2001 | Merry et al. |
| 6,339,720 B1 | 1/2002 | Anzellini et al. |
| 6,340,306 B1 | 1/2002 | Daoud |
| 6,356,779 B1 | 3/2002 | Katzenmaier et al. |
| 6,358,083 B1 | 3/2002 | Kraft |
| 6,360,119 B1 | 3/2002 | Roberts |
| 6,363,272 B1 * | 3/2002 | Combs ................ A61B 5/0448 439/668 |
| 6,364,685 B1 | 4/2002 | Manning |
| 6,383,010 B1 | 5/2002 | Mayo et al. |
| 6,383,011 B2 | 5/2002 | Chen |
| 6,383,036 B1 | 5/2002 | Steinhauser et al. |
| 6,386,917 B1 | 5/2002 | Sakaguchi |
| 6,393,317 B1 | 5/2002 | Fukuda |
| 6,394,953 B1 | 5/2002 | Devlin et al. |
| 6,398,575 B1 | 6/2002 | Bresson |
| 6,398,577 B1 | 6/2002 | Simmel et al. |
| 6,400,977 B1 | 6/2002 | Kelly et al. |
| 6,411,834 B1 | 6/2002 | Nagai |
| 6,413,112 B2 | 7/2002 | Semmeling et al. |
| 6,415,169 B1 | 7/2002 | Kornrumpf et al. |
| 6,419,636 B1 | 7/2002 | Young et al. |
| 6,434,410 B1 | 8/2002 | Cordero et al. |
| 6,447,170 B1 | 9/2002 | Takahashi et al. |
| 6,453,186 B1 | 9/2002 | Lovejoy et al. |
| 6,454,577 B1 | 9/2002 | Yi |
| 6,454,590 B1 | 9/2002 | Goodrich et al. |
| 6,454,605 B1 | 9/2002 | Bassler et al. |
| 6,456,872 B1 | 9/2002 | Faisander |
| 6,461,179 B1 | 10/2002 | Sullivan et al. |
| 6,487,430 B1 * | 11/2002 | Henderson ........... A61B 5/0416 439/909 |
| 6,494,744 B1 | 12/2002 | Lee |
| 6,514,099 B2 | 2/2003 | Endo |
| 6,517,372 B1 | 2/2003 | Jones |
| 6,531,657 B1 | 3/2003 | Jones, Jr. et al. |
| 6,533,600 B1 | 3/2003 | Kashiyama et al. |
| 6,540,549 B2 | 4/2003 | Rupert |
| 6,551,117 B2 | 4/2003 | Poplawski et al. |
| 6,553,246 B1 | 4/2003 | Wenger |
| 6,553,250 B2 | 4/2003 | Rantala |
| 6,558,189 B2 | 5/2003 | Groebe et al. |
| 6,561,834 B2 | 5/2003 | Chen |
| 6,564,079 B1 | 5/2003 | Cory et al. |
| 6,565,388 B1 | 5/2003 | Van Woensel et al. |
| 6,567,680 B2 | 5/2003 | Swetlik et al. |
| 6,575,759 B1 | 6/2003 | Ollivier |
| 6,575,794 B1 | 6/2003 | Nakamura |
| 6,582,252 B1 | 6/2003 | Lin |
| 6,589,066 B1 | 7/2003 | Wu |
| 6,592,391 B1 | 7/2003 | Wu |
| 6,592,404 B2 | 7/2003 | Endo |
| 6,604,963 B2 | 8/2003 | Lin |
| 6,607,397 B1 | 8/2003 | Zhang et al. |
| 6,609,018 B2 | 8/2003 | Cory et al. |
| 6,609,833 B1 | 8/2003 | Miyachi et al. |
| 6,611,705 B2 | 8/2003 | Hopman et al. |
| 6,612,860 B2 | 9/2003 | Droesbeke |
| 6,619,976 B2 | 9/2003 | Huetter et al. |
| 6,619,989 B1 | 9/2003 | Yi |
| 6,623,312 B2 | 9/2003 | Merry et al. |
| 6,636,754 B1 | 10/2003 | Baura et al. |
| 6,647,286 B1 | 11/2003 | Kato et al. |
| 6,648,665 B1 | 11/2003 | Wu |
| 6,648,666 B1 | 11/2003 | Wu |
| 6,654,626 B2 | 11/2003 | Devlin et al. |
| 6,655,979 B1 | 12/2003 | Lee |
| 6,659,790 B1 | 12/2003 | Wu |
| 6,663,412 B2 | 12/2003 | Aramoto et al. |
| 6,663,419 B2 | 12/2003 | Vaden |
| 6,663,420 B1 | 12/2003 | Xiao |
| 6,663,570 B2 | 12/2003 | Mott et al. |
| 6,669,510 B2 | 12/2003 | Yamawaki et al. |
| 6,688,894 B2 | 2/2004 | Knox, Jr. et al. |
| 6,688,907 B2 | 2/2004 | Yamaoka et al. |
| 6,702,602 B2 | 3/2004 | Wu |
| 6,702,603 B2 | 3/2004 | Wu |
| 6,702,616 B1 | 3/2004 | Chang et al. |
| 6,709,284 B1 | 3/2004 | Avlonitis |
| 6,716,165 B1 | 4/2004 | Flanders et al. |
| 6,722,912 B2 | 4/2004 | Wu |
| 6,736,650 B1 | 5/2004 | Chen |
| 6,743,053 B2 | 6/2004 | Wu |
| 6,748,797 B2 | 6/2004 | Breed et al. |
| 6,751,493 B2 | 6/2004 | Wenger |
| 6,755,689 B2 | 6/2004 | Zhang et al. |
| 6,768,921 B2 | 7/2004 | Organ et al. |
| 6,773,293 B1 | 8/2004 | Lee |
| 6,780,065 B2 | 8/2004 | Schwarz |
| 6,786,755 B2 | 9/2004 | Dambach et al. |
| 6,786,764 B2 | 9/2004 | Sivertsen |
| D498,535 S | 11/2004 | Genau et al. |
| 6,816,744 B2 | 11/2004 | Garfield et al. |

(56) References Cited

U.S. PATENT DOCUMENTS

| | | |
|---|---|---|
| 6,832,928 B2 | 12/2004 | Suzuki et al. |
| 6,837,734 B2 | 1/2005 | Ushlo et al. |
| 6,847,836 B1 | 1/2005 | Sujdak |
| 6,848,926 B2 | 2/2005 | Ling et al. |
| 6,851,969 B2 | 2/2005 | Archuletta |
| 6,860,750 B1 | 3/2005 | Wu |
| 6,866,535 B2 | 3/2005 | Uchida |
| 6,881,098 B2 | 4/2005 | Jeansonne et al. |
| 6,891,379 B2 | 5/2005 | Kelly et al. |
| 6,913,482 B1 | 7/2005 | Wu |
| 6,939,158 B2 | 9/2005 | Moffett et al. |
| 6,939,345 B2 | 9/2005 | Knight et al. |
| 6,945,796 B2 | 9/2005 | Bassler et al. |
| 6,945,807 B1 | 9/2005 | Wu |
| 6,948,973 B1 | 9/2005 | Hsu et al. |
| 6,970,731 B1 | 11/2005 | Jayaraman et al. |
| 6,973,341 B2 | 12/2005 | Watson |
| 6,973,343 B2 | 12/2005 | Wenger |
| 6,980,852 B2 | 12/2005 | Jersey-Willuhn et al. |
| 6,984,143 B2 | 1/2006 | Roese |
| D516,217 S | 2/2006 | Brown et al. |
| 6,997,733 B2 | 2/2006 | Peng |
| 7,004,787 B2 | 2/2006 | Milan |
| 7,008,255 B1 | 3/2006 | Wang |
| 7,025,618 B2 | 4/2006 | Fukuda |
| 7,025,628 B2 | 4/2006 | LaMeres et al. |
| 7,029,286 B2 | 4/2006 | Hall et al. |
| 7,033,207 B2 | 4/2006 | Nimura |
| 7,041,918 B1 | 5/2006 | Wu |
| 7,056,134 B2 | 6/2006 | Martin et al. |
| 7,056,141 B2 | 6/2006 | Moffett et al. |
| 7,077,711 B1 | 7/2006 | Moore |
| 7,081,008 B2 | 7/2006 | Tan |
| 7,081,026 B2 | 7/2006 | Schwarz |
| 7,083,480 B2 * | 8/2006 | Silber ................ A61B 5/04085 439/268 |
| 7,085,598 B2 | 8/2006 | Sato |
| 7,104,801 B1 | 9/2006 | Brodnick et al. |
| 7,110,804 B2 | 9/2006 | Baumer et al. |
| 7,117,590 B2 | 10/2006 | Koenig et al. |
| 7,118,411 B2 | 10/2006 | Huang et al. |
| 7,127,279 B2 | 10/2006 | Finneran et al. |
| 7,128,600 B2 | 10/2006 | Osypka |
| 7,134,908 B2 | 11/2006 | Wu |
| 7,137,839 B2 | 11/2006 | Dilliner et al. |
| 7,144,268 B2 | 12/2006 | Koenig et al. |
| 7,150,655 B2 | 12/2006 | Mastrototaro et al. |
| D535,029 S | 1/2007 | McAtamney et al. |
| 7,160,136 B2 | 1/2007 | Zhang et al. |
| 7,169,107 B2 | 1/2007 | Jersey-Willuhn et al. |
| 7,179,111 B2 | 2/2007 | Van Der Mee et al. |
| 7,179,113 B2 | 2/2007 | Koenig et al. |
| 7,182,630 B1 | 2/2007 | Su |
| 7,184,820 B2 | 2/2007 | Jersey-Willuhn et al. |
| 7,189,097 B2 | 3/2007 | Benham |
| 7,197,357 B2 | 3/2007 | Istvan et al. |
| 7,198,502 B2 | 4/2007 | Koenig et al. |
| 7,201,599 B2 | 4/2007 | Holub |
| 7,207,825 B2 | 4/2007 | Le Gallic et al. |
| 7,214,107 B2 * | 5/2007 | Powell .................. H01R 11/22 439/729 |
| 7,236,825 B2 | 6/2007 | Wang |
| 7,252,542 B2 | 8/2007 | Chen |
| 7,252,556 B2 | 8/2007 | Anbo et al. |
| 7,252,565 B2 | 8/2007 | Hunter |
| 7,255,609 B1 | 8/2007 | Epstein |
| 7,258,566 B2 | 8/2007 | Koenig et al. |
| 7,264,510 B2 | 9/2007 | Koenig et al. |
| 7,270,568 B2 | 9/2007 | Osypka |
| 7,270,580 B2 | 9/2007 | Bradley et al. |
| 7,272,427 B2 | 9/2007 | Ristolainen |
| 7,272,428 B2 | 9/2007 | Hopman et al. |
| 7,275,951 B2 | 10/2007 | Shigeta et al. |
| 7,281,937 B2 | 10/2007 | Reed et al. |
| 7,287,998 B2 | 10/2007 | Masai |
| 7,303,430 B2 | 12/2007 | Butcher |
| 7,318,740 B1 | 1/2008 | Henry et al. |
| 7,319,895 B2 | 1/2008 | Klefstad-Sillinville et al. |
| 7,322,849 B2 | 1/2008 | Sutton |
| 7,329,139 B2 | 2/2008 | Benham |
| 7,333,850 B2 | 2/2008 | Marossero et al. |
| 7,347,710 B2 | 3/2008 | Ohtaka et al. |
| 7,347,826 B1 | 3/2008 | Karicherla et al. |
| 7,359,751 B1 | 4/2008 | Erickson et al. |
| 7,361,058 B1 | 4/2008 | Lien et al. |
| 7,364,440 B2 | 4/2008 | Gobron et al. |
| 7,371,102 B2 | 5/2008 | Sakamoto et al. |
| 7,373,196 B2 | 5/2008 | Ryu et al. |
| 7,374,448 B1 | 5/2008 | Jepsen et al. |
| 7,381,082 B2 | 6/2008 | Lai |
| 7,390,224 B2 | 6/2008 | Sodemann et al. |
| 7,396,246 B2 | 7/2008 | Okada et al. |
| 7,399,195 B2 | 7/2008 | Kim et al. |
| 7,401,946 B2 | 7/2008 | Laukhuf |
| 7,402,071 B2 | 7/2008 | Ohtaka et al. |
| 7,413,461 B2 | 8/2008 | Dawiedczyk et al. |
| 7,413,485 B2 | 8/2008 | Lappoehn |
| 7,416,440 B2 | 8/2008 | Homyk et al. |
| 7,422,437 B1 | 9/2008 | Lin et al. |
| 7,422,452 B2 | 9/2008 | Achtner et al. |
| 7,445,512 B1 | 11/2008 | Lai |
| 7,445,522 B2 | 11/2008 | Burns |
| 7,462,074 B1 | 12/2008 | Devlin et al. |
| 7,473,141 B2 | 1/2009 | Liao |
| 7,488,187 B2 | 2/2009 | Wolf |
| 7,494,383 B2 | 2/2009 | Cohen et al. |
| 7,497,738 B2 | 3/2009 | Kuo |
| 7,503,807 B2 | 3/2009 | Martin et al. |
| 7,556,535 B2 | 7/2009 | Liao |
| 7,581,992 B1 | 9/2009 | Liu et al. |
| 7,585,182 B2 | 9/2009 | Asante et al. |
| 7,591,673 B2 | 9/2009 | Chan et al. |
| 7,604,511 B1 | 10/2009 | Johnson |
| 7,618,377 B2 | 11/2009 | McAtamney et al. |
| 7,632,130 B2 | 12/2009 | Sami |
| D609,813 S | 2/2010 | Molden et al. |
| 7,666,028 B2 | 2/2010 | Meleck |
| D629,358 S | 12/2010 | Slippy et al. |
| 7,950,971 B2 * | 5/2011 | Hobet .................. A61B 5/0408 439/822 |
| 8,038,484 B2 | 10/2011 | Selvitelli et al. |
| 8,152,571 B2 * | 4/2012 | Selvitelli et al. ............. 439/729 |
| 8,255,041 B2 | 8/2012 | Istvan et al. |
| D675,738 S | 2/2013 | Baumer et al. |
| 8,408,507 B2 | 4/2013 | Liu |
| 8,408,948 B2 | 4/2013 | Selvitelli et al. |
| 8,414,315 B2 | 4/2013 | Dekoski |
| D689,614 S | 9/2013 | Browne et al. |
| D699,360 S | 2/2014 | Marzynski et al. |
| 8,690,611 B2 | 4/2014 | Selvitelli et al. |
| 8,694,080 B2 | 4/2014 | Farrior |
| 8,795,004 B2 | 8/2014 | Selvitelli et al. |
| D718,867 S | 12/2014 | Schroderus |
| 2001/0053639 A1 | 12/2001 | Endo |
| 2002/0133069 A1 | 9/2002 | Roberts |
| 2002/0138011 A1 | 9/2002 | Rantala |
| 2002/0188216 A1 | 12/2002 | Kayyali et al. |
| 2003/0068914 A1 | 4/2003 | Merry et al. |
| 2003/0068918 A1 | 4/2003 | Christensson |
| 2004/0073127 A1 | 4/2004 | Istvan et al. |
| 2004/0127802 A1 | 7/2004 | Istvan et al. |
| 2004/0176674 A1 | 9/2004 | Nazeri |
| 2004/0203273 A1 | 10/2004 | Schwarz |
| 2005/0164551 A1 | 7/2005 | Wlos |
| 2005/0177052 A1 | 8/2005 | Istvan et al. |
| 2005/0203349 A1 | 9/2005 | Nanikashvili |
| 2006/0004273 A1 | 1/2006 | Lobodzinski |
| 2006/0073728 A1 | 4/2006 | Zaiken et al. |
| 2006/0110962 A1 * | 5/2006 | Powell .................. H01R 11/22 439/169 |
| 2006/0286861 A1 | 12/2006 | Avevor et al. |
| 2007/0038057 A1 | 2/2007 | Nam et al. |
| 2007/0260133 A1 | 11/2007 | Meyer |
| 2008/0132106 A1 | 6/2008 | Burnes et al. |

(56) References Cited

U.S. PATENT DOCUMENTS

| | | | |
|---|---|---|---|
| 2008/0132773 | A1 | 6/2008 | Burnes et al. |
| 2008/0177168 | A1 | 7/2008 | Callahan et al. |
| 2009/0099423 | A1 | 4/2009 | Al-Ali et al. |
| 2009/0149731 | A1 | 6/2009 | Selvitelli et al. |
| 2009/0221153 | A1 | 9/2009 | Santangelo et al. |
| 2011/0092833 | A1 | 4/2011 | Farrior |
| 2011/0275252 | A1 | 11/2011 | Selvitelli et al. |
| 2012/0196474 | A1 | 8/2012 | Selvitelli et al. |
| 2013/0023750 | A1 | 1/2013 | Callahan et al. |
| 2013/0189881 | A1 | 7/2013 | Selvitelli et al. |
| 2014/0170896 | A1 | 6/2014 | Selvitelli et al. |
| 2014/0180148 | A1 | 6/2014 | Coggins et al. |

FOREIGN PATENT DOCUMENTS

| | | |
|---|---|---|
| DE | 9002539 U1 | 5/1990 |
| DE | 10225621 | 1/2004 |
| DE | 102004032410 | 1/2006 |
| EP | 0 766 946 A2 | 4/1997 |
| EP | 0 799 628 | 10/1997 |
| EP | 1 050 269 | 11/2000 |
| EP | 1645224 | 4/2008 |
| EP | 1 932 470 | 6/2008 |
| EP | 2 070 474 | 6/2009 |
| GB | 162804 | 5/1921 |
| JP | 10248820 A | 9/1998 |
| JP | 2003/010138 | 1/2003 |
| JP | 2004/282608 | 10/2004 |
| WO | WO 03 047 427 | 6/2003 |
| WO | WO 2008/092098 A2 | 7/2008 |
| WO | WO 2013/013370 A1 | 1/2013 |

OTHER PUBLICATIONS

Chinese Office Action dated Jan. 12, 2015; with English Translation for Chinese App. No. 200180072455.9; 15 pages.
A&D Company, Limited, "Vital Sensor Graphic Model", No. TM-2560G/TM2564G-TM-2564GP/TM2564GP, Jan. 1, 2004; pp. 1-62.
Andreas Boos et al.; "A New Lightweight Fetal Telemetry System", Dec. 1995; Hewlett-Packard Journal; 12 pages.
Tyco Healthcare Kendal, ECG Electrodes Where Quality leads 2003 8 pages.
European Search Report Corresponding to European Application No. EP 07 25 3850, Date of completion is Dec. 21, 2007 3 pages.
EP Notice Under Rule161 dated Feb. 28, 2014, for EP App. No, 11869957.8 3 pages.
Response to Written Opinion and Claims filed on Jun. 11, 2014, for EP App. No. 11869957.8 6 pages.
Search Report and Written Opinion dated Apr. 12, 2012, for App. No. PCT/CN2011/077508 14 pages.
First Office Action dated Jul. 26, 2011, for Chinese App. No. 200810191090.1 6 pages.
Letter regarding Response to Office Action dated Nov. 22, 2011, for Chinese App. No. 200810191090.1 9 pages.
Response to Office Action dated Dec. 12, 2011, for Chinese App. No. 200810191090.1 18 pages.
Letter dated May 11, 2012 enciosirig Second Office Action dated Apr. 27, 2012, for Chinese App. No. 200810191090.1 6 pages.
Notification of Response to Second Office Action dated Jun. 11, 2012, for Chinese App. No. 200810191090.1 5 pages.
Letter dated Dec. 20, 2012 enclosing Grant Notification dated Dec. 19, 2012, for Chinese App. No. 200810191090.1 4 pages.
Divisional Application as filed on Mar. 1, 2013, for Chinese App. No. 200810191090.1 37 pages.
European Office Action dated Nov. 19, 2010, for EP App. No. 08171185.5 1 page.
Letter dated Dec. 22, 2010 in response to EP Office Action Nov. 19, 2010 European Office Action for EP App. No. 08171185.5 1 page.
Response to Office Action dated Oct. 3, 2012 for EP App. No. 08171185.5 2 page.
Letter dated Oct. 4, 2012 and copy of Divisional for EP App. No. 08171185.5 39 pages.
Letter dated Dec. 16, 2013 in response to Communication dated Jun. 24, 2013, for EP App. No. 08171185.5 4 pages.
Examination Report dated Jun. 24, 2013, for EP App. No. 08171185.5 4 pages.
Extended Search Report dated Mar. 7, 2012, for EP App. No. 08171185.5 8 pages.
Letter dated Apr. 2, 2012 and Office Action for Mexican App. No. MX/a/2008/015927 3 pages.
Letter dated May 15, 2012 and Response to Office Action for Mexican App. No. MX/a/2008/015927 filed on Dec. 11, 2008 9 Pages.
Letter dated Jun. 26, 2012 and Regarding Notice of Allowance with allowed claims for Mexican App. No. MX/a/2008/015927 filed on Dec. 11, 2008 7 Pages.
Letter dated Feb. 5, 2014 Confirming receipt of Notice of Allowance. for Mexican App. No. MX/a/2012/009542 2 pages.
Letter dated Feb. 25, 2013 also enclosing Office Action fpr App. No. MX/a/2012/009542 3 pages.
Letter and Response to Office Action dated Apr. 23, 2013, for Mexican App. No. MX/a/2012/009542 20 pages.
Letter dated Sep. 18, 2013 and Office Action for Mexican App. No. MX/a/2012/009542 4 pages.
Letter dated Oct. 30, 2013 and Response to Office Action for App. No. MX/a/2012/009542 5 pages.
Letter dated Jun. 10, 2014 Confirming receipt of Notice of Allowance for Mexican App. No. MX/a/2013/012636 2 pages.
Letter dated Jun. 10, 2014 Confirming receipt of Notice of Allowance for Mexican App. No. MX/a/2013/012635 2 pages.
Extended Search Report dated Oct. 8, 2013, for EP App. No. 12187209.7009542 6 pages.
European Notice Responding to Search Report dated Nov. 11, 2013, for EP App. No. 12187209.7009542 2 pages.
Exam Report dated Mar. 11, 2014, for EP App. No. 12187209.7009542 4 pages.
Response dated Jan. 27, 2014 to Extended Search Report dated Oct. 8, 2013, for EP App. No. 12187209.7009542 16 pages.
Response to Exam Report dated Jun. 24, 2014 for EP App. No. 12187209.7009542 8 pages.
Response dated Nov. 2, 2011 to Communication dated May 10, 2011 for EP App. No. 10013624.10 5 pages.
Extended Search Report dated Apr. 4, 2011, for EP App. No. 10013624.10 14 pages.
European Exam Report dated Nov. 12, 2013, for EP App. No. 12187209.7009542 6 pages.
Response to Communication dated Mar. 17, 2014 for EP App. No. 12187209.7009542 14 pages.
European Office Action dated May 21, 2014, for EP App. No. 12187209.7009542 5 pages.
European Search Report dated May 23, 2014, for EP App. No. 14162076.5 10 pages.
Response to Chinese Office Action dated May 4, 2011, for Chinese App. No. 201010624971.50 21 pages.
Notification of Entry into Examination Procedure dated Oct. 11, 2012, for Chinese App. No. 201010624971.50 2 Pages.
Receipt of First Office Action dated Nov. 28, 2013, for Chinese App. No. 201010624971.50 136 Pages.
Response to Office Action dated Apr. 14, 2014, for Chinese App. No. 201010624971.50 34 Pages.
Search Report dated Jun. 4, 2014, for App. No. PCT/US2014/019479 10 pages.
Letter and Chinese Office Action dated Jul. 1, 2014, for Chinese App. No. 2013100649128.3 38 pages.
Callahan U.S. Appl. No. 13/987,326, flied Mar. 15, 2013 37 pages.
Farrier U.S. Appl. No. 14/198,140, flied Mar. 3, 2014 44 pages.
Simpson U.S. Appl. No. 14/209,278, filed on Mar. 13, 2014 21 pages.
Selvitelli U.S. Appl. No. 7/324,380, filed on Jul. 7, 2014 26 pages.
U.S. Appl. No. 12/330,550; 175 Pages.
U.S. Appl. No. 13/182,656; 143 Pages.
U.S. Appl. No. 13/443,096; 50 Pages.
U.S. Appl. No. 13/785,713, filed Mar. 5, 2013, 200pages, Part 1.
U.S. Appl. No. 13/785,713, filed Mar. 5, 2013, 200 pages, Part 2.
U.S. Appl. No. 13/785,713, filed Mar. 5, 2013, 200 pages, Part 3.

(56) References Cited

OTHER PUBLICATIONS

U.S. Appl. No. 13/785,713, filed Mar. 5, 2013, 200 pages, Part 4.
U.S. Appl. No. 13/785,713, filed Mar. 5, 2013, 200 pages, Part 5.
U.S. Appl. No. 13/785,713, filed Mar. 5, 2013, 200 pages, Part 6.
U.S. Appl. No. 13/785,713, filed Mar. 5, 2013, 200 pages, Part 7.
U.S. Appl. No. 13/785,713, filed Mar. 5, 2013, 200 pages, Part 8.
U.S. Appl. No. 13/785,713, filed Mar. 5, 2013, 200 pages, Part 9.
U.S. Appl. No. 13/785,713, filed Mar. 5, 2013, 200 pages, Part 10.
U.S. Appl. No. 13/785,713, filed Mar. 5, 2013, 200 pages, Part 11.
U.S. Appl. No. 13/785,713, filed Mar. 5, 2013, 200 pages, Part 12.
U.S. Appl. No. 13/785,713, filed Mar. 5, 2013, 200 pages, Part 13.
U.S. Appl. No. 13/785,713, filed Mar. 5, 2013, 18 pages, Part 14.
U.S. Appl. No. 14/041,471; Part 1 of 16; 350 Pages.
U.S. Appl. No. 14/041,471; Part 2 of 16; 350 Pages.
U.S. Appl. No. 14/041,471; Part 3 of 16; 350 Pages.
U.S. Appl. No. 14/041,471; Part 4 of 16; 350 Pages.
U.S. Appl. No. 14/041,471; Part 5 of 16; 350 Pages.
U.S. Appl. No. 14/041,471; Part 6 of 16; 350 Pages.
U.S. Appl. No. 14/041,471; Part 7 of 16; 350 Pages.
U.S. Appl. No. 14/041,471; Pat 8 of 16; 350 Pages.
U.S. Appl. No. 14/041,471; Part 9 of 16; 350 Pages.
U.S. Appl. No. 14/041,471; Part 10 of 16; 350 Pages.
U.S. Appl. No. 14/041,471; Part 11 of 16; 350 Pages.
U.S. Appl. No. 14/041,471; Part 12 of 16; 350 Pages.
U.S. Appl. No. 14/041,471; Part 13 of 16; 350 Pages.
U.S. Appl. No. 14/041,471, Part 13 of 16; 350 Pages.
U.S. Appl. No. 14/041,471 Part 13 of 16; 129 Pages.
U.S. Appl. No. 12/876,316; Part 1 of 5; 250 Pages.
U.S. Appl. No. 12/876,316; Part 2 of 5; 250 Pages.
U.S. Appl. No. 12/876,316; Part 3 of 5; 250 Pages.
U.S. Appl. No. 12/876,316; Part 4 of 5; 250 Pages.
U.S. Appl. No. 12/876,316; Part 5 of 5; 238 Pages.
International Search Report and Written Opinion dated Sep. 9, 2014 for PCT Application No. PCT/US2014/027328; 16 pages.
Office Acton dated Sep. 10, 2014 for U.S. Appl. No. 14/324,380; 7 pages.
Preliminary Amendment dated Jul. 7, 2014 for U.S. Appl. No. 14/324,380 6 pages.
Voluntary Amendment with English claims dated Jul. 15, 2014 for Application No. 201180072455.9 7 pages.
Response to Chinese Office Action filed Oct. 24, 2014 with English translation for Chinese Application No. 201310064924.3; 27 pages.
Letter from CCPIT Patent and Trademark Law Office dated Jan. 2, 2015 for Chinese Appiication No. 201310064924.3, 7 pages.
Chinese Office Action dated Nov. 17, 2014 for Chinese Application No. 201310064924.3, 3 pages.
European Extended Search Report dated Nov. 18, 2014 for European Appilcation No. 11869957.8; 9 pages.
Response to Office Action filed Oct. 24, 2014 for U.S. Appl. No. 13/987,326; 8 pages.
Notice of Allowance dated Nov. 18, 2014 for U.S. Appl. No. 13/987,326; 4 pages.
Partial Search Report dated Jun. 5, 2014 for Application No. PCT/US2014/027328 6 pages.
U.S Appl. No. 13/987,326; 90 Pages.
Simpson U.S. Appl. No. 14/209,273, filed Mar. 13, 2014 30 pages.
Farrior U.S. Appl. No. 14/195,140, filed Mar. 3, 2014 70 pages.
Selviteill U.S. Appl. No. 14/324,380, filed Jul. 7, 2014 41 pages.
Notice of Allowance dated Mar. 30, 2015 for U.S. Appl. No. 13/987,326; 7 pages.
Notice of Allowance dated Mar. 31, 2015 for U.S. Appl. No. 14/324,380; 9 pages.
European Search Report dated Apr. 17, 2015 for European Application No. 14197698.5; 7 pages.
Notice of Allowance fated Jun. 25, 2015 for U.S. Appl. No. 14/324,380; 5 pages.
Notice of Allowance dated Jul. 17, 2015 for U.S. Appl. No. 13/987,326; 7 pages.
International Preliminary Report on patentability dated Jan. 28, 2014 for PCT Application No. PCT/CN2011/077506; 8 pages.
Office Action dated May 4, 2015 for Canadian Application No. 2,646,037; 4 pages.
Restriction Requirement dated Aug. 6, 2015 for U.S. Appl. No. 14/209,278; 5 pages.
Office Action dated Jul. 23, 2015 for Chinese Application No. 201180072455.9; 7 pages.
Notice of Allowance dated May 15, 2015 corresponding to U.S. Appl. No. 29/486,095; 25 Pages.
Notification to Grant dated May 25, 2015 for Chinese Application No. 201310064924.3; 5 pages.
Notice of Allowance dated Apr. 23, 2015 for European Application No. 12187209.7; 39 pages.
Communication Pursuant to Rules 70(2) and 70a(2) EPC and reference to Rule 39(1) EPC dated May 26, 2015 for European Application No. 14197698.5; 2 pages.
U.S. Appl. No. 14/041,484; 101 pages.
Response to Office Action filed on Oct. 23, 2014 for U.S. Appl. No. 13/987,326; 8 pages.
Office Action dated Aug. 6, 2014 for Chinese Application No. 201010624971.5; 17 pages.
Office Action dated Jun. 26, 2014 for Australian Application No. 2010235901, 4 pages.
Response to office action filed Jun. 1, 2015 for European Application No. 11869957.8; 10 pages.
Response to Office Action with English translation filed Feb. 2, 2015 for Chinese Application No. 201310064924.3; 23 pages.
Response to Office Action with English translation filed May 27, 2015 for Chinese Application No. 201180072455.9; 15 pages.
Ex Parte Quayle Action dated Aug. 14, 2015 corresponding to U.S. Appl. No. 29/498,717; 38 pages.
Response to office action filed Aug. 7, 2015 for European Application No. 14197698.5; 27 pages.
Office Action dated Aug. 17, 2015 for Canadian Application No. 2841601, 5 pages.
PCT International Preliminary Report on Patentability and Written Opinion of the ISA dated Sep. 24, 2015; for PCT App. No. PCT/US2014/027328; 12 pages.
PCT International Preliminary Report on Patentability and Written Opinion of the ISA dated Sep. 24, 2015; for PCT App. No. PCT/US2014/019479; 8 pages.
Letter from CCPIT Patent and Trademark Law Office dated Aug. 6, 2015, and Chinese Office Action with English translation dated Jul. 23, 2015; for Chinese Pat. App. No. 201180072455.9; 9 pages.
Letter from CCPIT Patent and Trademark Law Office dated Sep. 30, 2015, and Response dated Sep. 29, 2015 to Chinese Office Action dated Jul. 23, 2015; for Chinese Pat. App. No. 201180072455.9; 3 pages.
Letter from CCPIT Patent and Trademark Law Office dated Nov. 9, 2015, and Chinese Decision to Grant dated Nov. 5, 2015; for Chinese Pat. App. No. 201180072455.9; 5 pages.
Notice of Allowance dated Oct. 29, 2015 for U.S. Appl. No. 13/987,326, 11 pages.
Summons to Attend Oral Proceedings Pursuant to Rule 115(1)EP dated Nov. 2, 2015 for European Application No. 08171185.5; 3 pages.
Response to Examiner's Report filed Nov. 4, 2015 for Canadian Application No, 2,646,037; 22 pages.
Office Action dated Dec. 17, 2015 for U.S. Appl. No. 14/209,278; 6 pages.
Response to Examiner's Report filed Nov. 30, 2015 for Canadian Application No, 2,841,601; 11 pages.
Amendment in Response to the Office Action dated Dec. 17, 2015, from U.S. Appl. No. 14/209,278, filed Mar. 16, 2016, 8 pages.

* cited by examiner

ECG ELECTRODE CONNECTOR

BACKGROUND

1. Technical Field

The present disclosure relates to biomedical electrodes, and in particular, to a radiolucent biomedical electrode connector and radiolucent lead wires for performing biomedical monitoring of a patent during imaging procedures.

2. Background of Related Art

Electrocardiograph (ECG) monitors are widely used to obtain medical (i.e. biopotential) signals containing information indicative of the electrical activity associated with the heart and pulmonary system. To obtain medical signals, ECG electrodes are applied to the skin of a patient in various locations. The electrodes, after being positioned on the patient, connect to an ECG monitor by a set of ECG lead wires. The distal end of the ECG lead wire, or portion closest to the patient, may include a connector which is adapted to operably connect to the electrode to receive medical signals from the body. The proximal end of the ECG lead set is operably coupled to the ECG monitor and supplies the medical signals received from the body to the ECG monitor.

A typical ECG electrode assembly may include an electrically conductive layer and a backing layer, the assembly having a patient contact side and a connector side. The contact side of the electrode pad may include biocompatible conductive gel or adhesive for affixing the electrode to a patient's body for facilitating an appropriate electrical connection between a patient's body and the electrode assembly. The connector side of the pad may incorporate a metallic press stud having a bulbous profile for coupling the electrode pad to the ECG lead wire. In use, the clinician removes a protective covering from the electrode side to expose the gel or adhesive, affixes the electrode pad to the patient's body, and attaches the appropriate ECG lead wire connector to the press stud by pressing or "snapping" the lead wire connector onto the bulbous press stud to achieve mechanical and electrical coupling of the electrode and lead wire. Alternatively, ECG connectors that engage via manipulation of a lever or other mechanical locking device may be employed. After use, a clinician then removes the ECG lead wire connector from the pad by pulling or "unsnapping" the connector from the pad or by releasing the lever or other locking mechanism.

Placement of the electrodes on a patient has been established by medical protocols. A common protocol requires the placement of the electrodes in a 5-lead configuration: one electrode adjacent each clavicle bone on the upper chest and a third electrode adjacent the patient's lower left abdomen, a fourth electrode adjacent the sternum, and a fifth electrode on the patient's lower right abdomen.

During certain procedures it may be necessary to monitor biological (e.g., ECG) parameters of a patient that is undergoing imaging, such as CT-scan or MRI. Use of conventional ECG connectors and lead wire sets typically associated therewith may have drawbacks in these applications, since they tend to interfere with the imaging systems. In one example, certain components of the ECG connectors and/or lead wires may be detected by the imaging apparatus and consequently may obfuscate the visual images upon which clinicians and surgeons rely. In another example, ferrous and/or magnetic components commonly found in ECG connectors, such as in springs and clips, may be potentially hazardous when used within the intense magnetic field of an MRI scanner.

SUMMARY

In an embodiment in accordance with the present disclosure, there is provided an ECG connector assembly, comprising a housing having an interior recessed surface. The interior recessed surface has disposed therein an opening dimensioned to operably receive the press stud of an ECG electrode pad. A radiolucent conductor is disposed on at least a portion of the interior recessed surface, and a radiolucent lead wire conductor extends from a proximal end of the housing and is operably coupled to the radiolucent conductor. The ECG connector assembly includes an engagement member pivotably disposed upon the interior recessed surface and having an engaging face and a pivot. The engagement member is pivotable between a first position whereby the engaging face is closer to a top portion of the opening and a second position whereby engaging face is further from a top portion of the opening. A radiolucent resilient member disposed within the housing is configured to bias the engagement member towards the first position.

BRIEF DESCRIPTION OF THE DRAWINGS

The accompanying drawings are not intended to be drawn to scales. In the drawing, each identical or nearly identical component that is illustrated in various figures is represented by a like numeral. For purposes of clarity, not every component may be labeled in every drawing. Various embodiments of the present disclosure are described hereinbelow with references to the drawings, wherein.

DETAILED DESCRIPTION OF EMBODIMENTS

Figure 1:
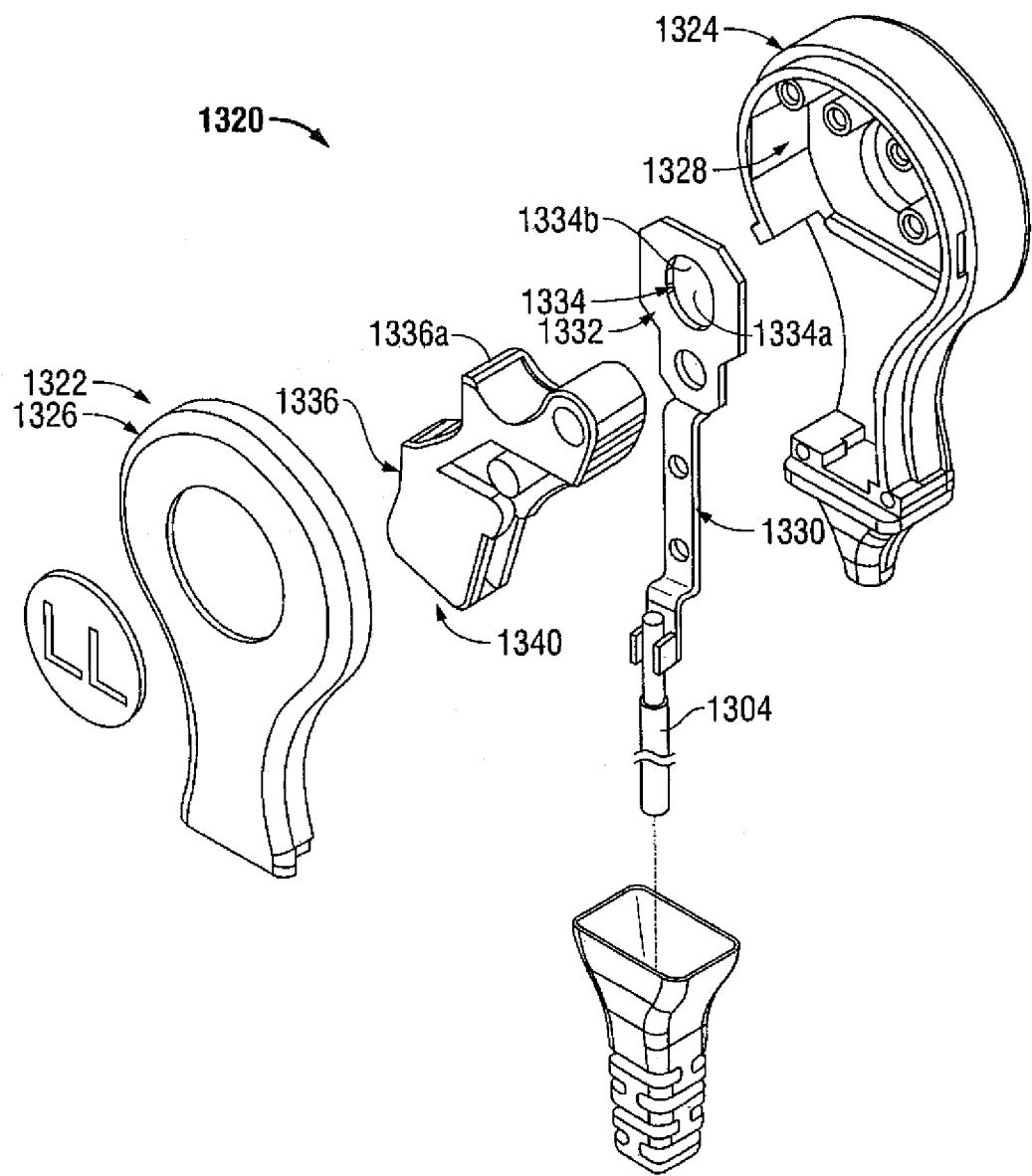
FIG. 1 is an exploded view of a conventional ECG electrode connector.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," "having," "continuing," or "involving" and variations thereof herein, is meant to encompass the items listed thereafter and equivalents thereof as well as additional items.

Particular embodiments of the present disclosure are described hereinbelow with reference to the accompanying drawings; however, the disclosed embodiments are merely examples of the disclosure, which may be embodied in various forms. Well-known functions or constructions and repetitive matter are not described in detail to avoid obscuring the present disclosure in unnecessary or redundant detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

In the drawings and in the descriptions that follow, the term "proximal," as is traditional, shall refer to the end of the instrument that is closer to a user, while the term "distal" shall refer to the end that is farther from a user. In addition, as used herein, terms referencing orientation, e.g., "top", "bottom", "up", "down", "left", "right", "clockwise", "counterclockwise", and the like, are used for illustrative purposes with reference to the figures and features shown therein. Embodiments in accordance with the present disclosure may be practiced in any orientation without limitation.

The present invention is directed to an electrode connector suitable for use during patient imaging, such as during a CT-scan or MRI. Commonly available electrode connectors have components which may be detected on the image and/or may become dangerous when exposed to a particular field, such as a magnetic field.

Figure 2:
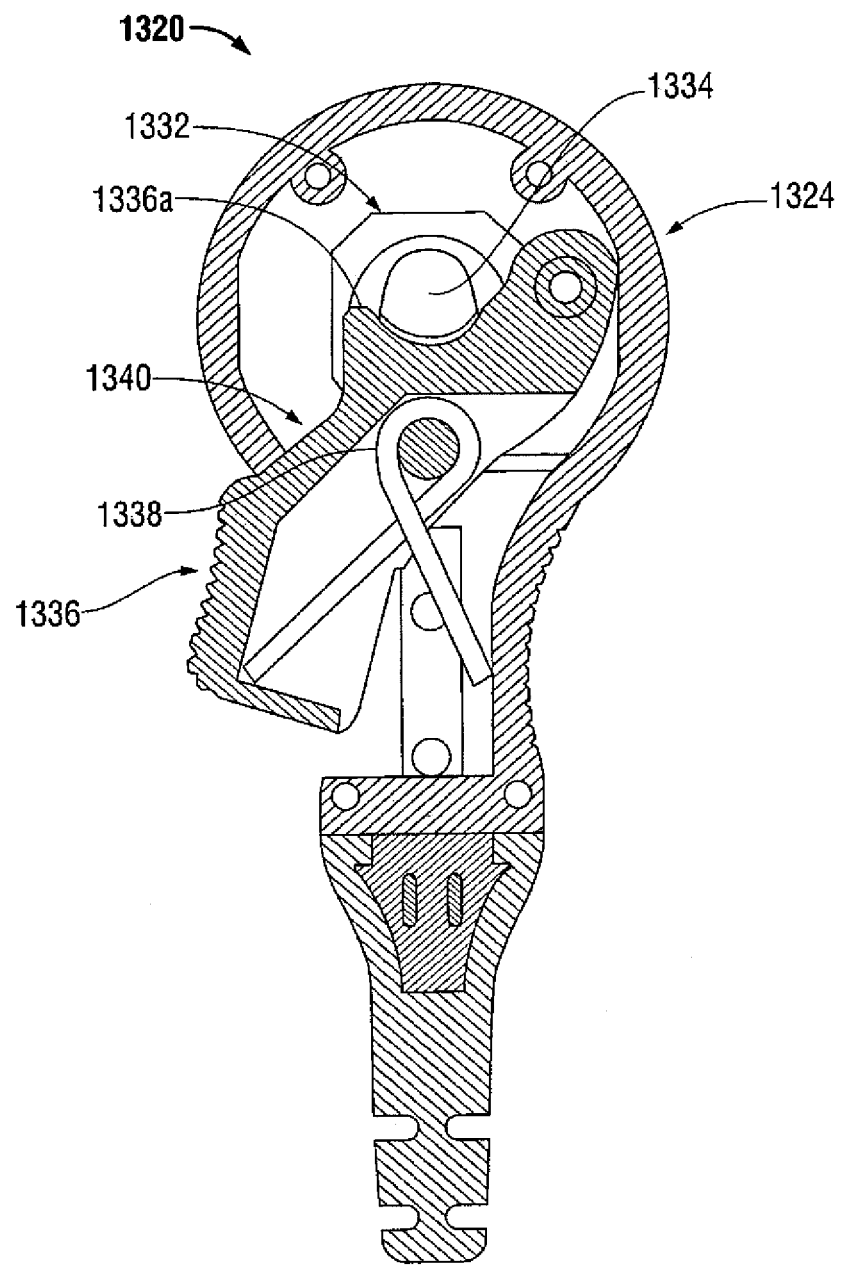
FIG. 2 is a schematic diagram of the conventional ECG electrode connector of FIG. 12A.

One embodiment of a conventional electrode connector 1320 is shown in FIG. 1 and FIG. 2 which includes a housing 1322 having an upper member 1324 and a lower member 1326, and defining an internal cavity 1328 therebetween. Housing 1322 is fabricated from a non-conducting material, e.g., an injection molded polymer which electrically insulates the subject from the conductive element(s) therewithin. Upper member 1324 and lower member 1326 are separate components attached to each other by any suitable method of bonding, such as without limitation, adhesive, ultrasonic welding, or heat welding. Upper member 1324 and lower member 1326 form a non-conductive element of the housing 1322.

Housing 1322 of the conventional electrode connector includes a lead wire terminal 1330 which is electrically connected to a respective end of lead wire 1304 by any suitable method of connection, including without limitation, crimping, soldering, or welding. Lead wire terminal 1330 is formed of a conductive material, typically a metal such as stainless steel. Housing 1322 supports a contact member 1332 also formed of a conductive material that is electrically connected to a lead wire. In one embodiment, the lead wire is formed of a conductive metals such as tinned copper. In another embodiment, the conductive material of the contact member is a metal such as stainless steel. Contact member 1332 and lead wire terminal 1330 may be integrally formed. Contact member 1332 defines a contact opening 1334 formed therein and in communication with internal cavity 1328 of housing 1322. Contact opening 1334 includes first contact opening portion 1334a and second contact opening portion 1334b. First contact opening portion 1334a defines an internal dimension or diameter which is greater than the corresponding internal dimension or diameter of second contact opening portion 1334b.

Housing 1322 of conventional electrode connector further includes a lever 1340 pivotably connected thereto. Lever 1340 includes an actuating end 1336. Lever 1340 is biased to a first position by a biasing member 1338, as shown in FIG. 2. Biasing member 1338 is formed of a resilient metal, such as stainless steel. Lever 1340 includes an engaging region 1336a projecting therefrom so as to extend across first contact opening portion 1334a of contact opening 1334 when lever 1340 is in the first position. In use, lever 1340 is actuatable to a second position wherein engaging region 1336a thereof does not obstruct or extend across first contact opening portion 1334a of contact opening 1334. For example, a clinician may apply finger pressure to actuating end 1336 that is sufficient to overcome the biasing force of biasing member 1338, thereby causing engaging region 1336a to move to a second position as herein described.

Conventional ECG electrode connector 1320 is adapted for connection to a conventional snap-type biomedical electrode (not explicitly shown). A typical snap-type biomedical electrode incorporates an electrode flange or base and male press stud or terminal extending in transverse relation to the electrode base. The male press stud terminal may have a bulbous head whereby an upper portion of the terminal has a greater cross-sectional dimension than a lower portion of the terminal. Accordingly, in use, when lever 1340 of electrode connector 1320 is in the second position, the head of the male press stud terminal of the snap-type biomedical electrode may be inserted into first contact opening portion 1334a of contact opening 1334 and actuating end 1336, and thus, lever 1340, may be released so that biasing member 1338 moves engaging region 1336a of lever 1340 against the head of the male press stud (not explicitly shown) to push or force the lower portion of the press stud into a second contact opening portion 1334b of contact opening 1334. The biasing force of biasing member 1338 helps to maintain the press stud within second contact opening portion 1334b of contact opening 1334 and thus inhibits removal or disconnection of the biomedical electrode from ECG connector 1320. However, because lead wire terminal 1330, contact member 1332 and biasing member 1338 are metallic, one or more of these components may be detected in the image and/or become dangerous when exposed to a magnetic filed.

Figure 3A:
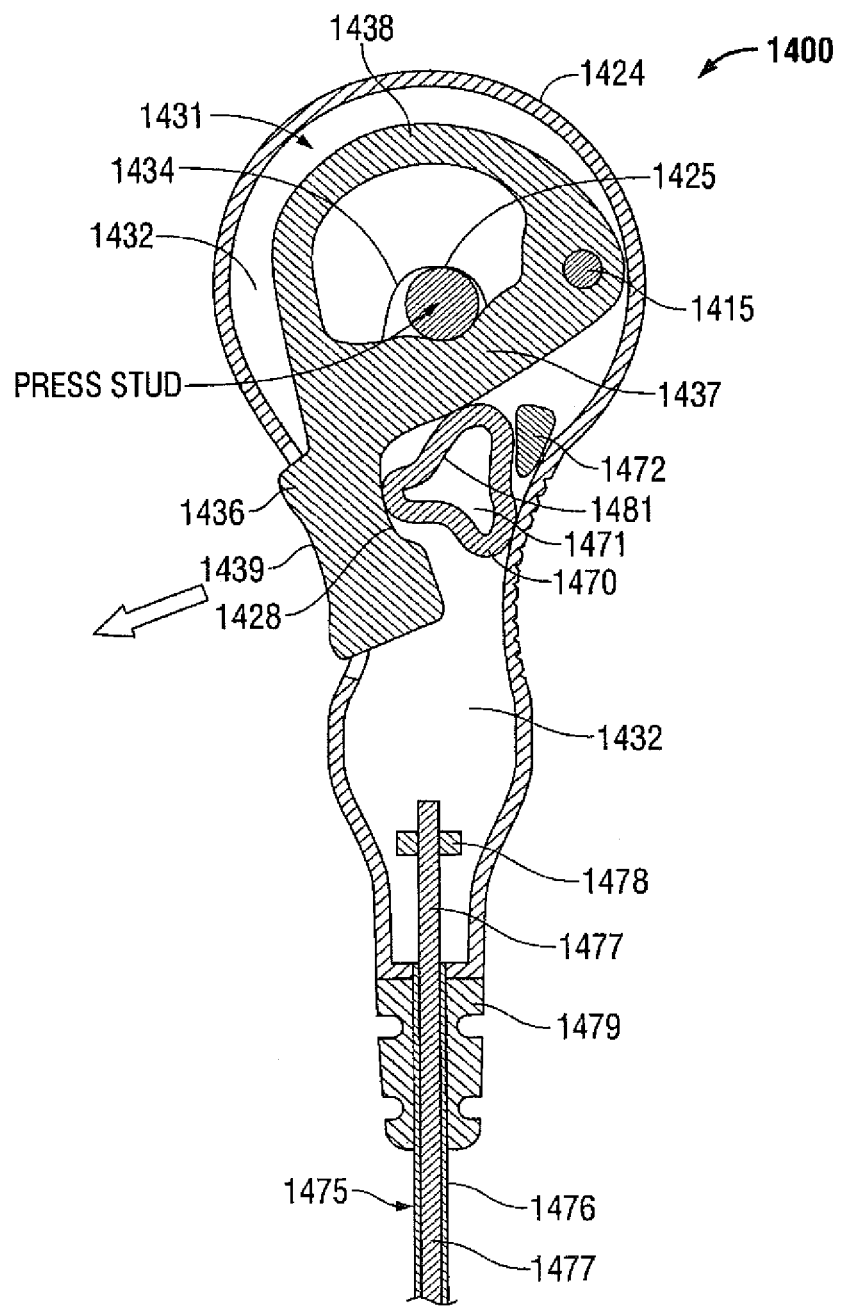
FIG. 3A is a view of an embodiment of a radiolucent ECG electrode connector in an engaged configuration in accordance with the present disclosure.
Figure 3B:
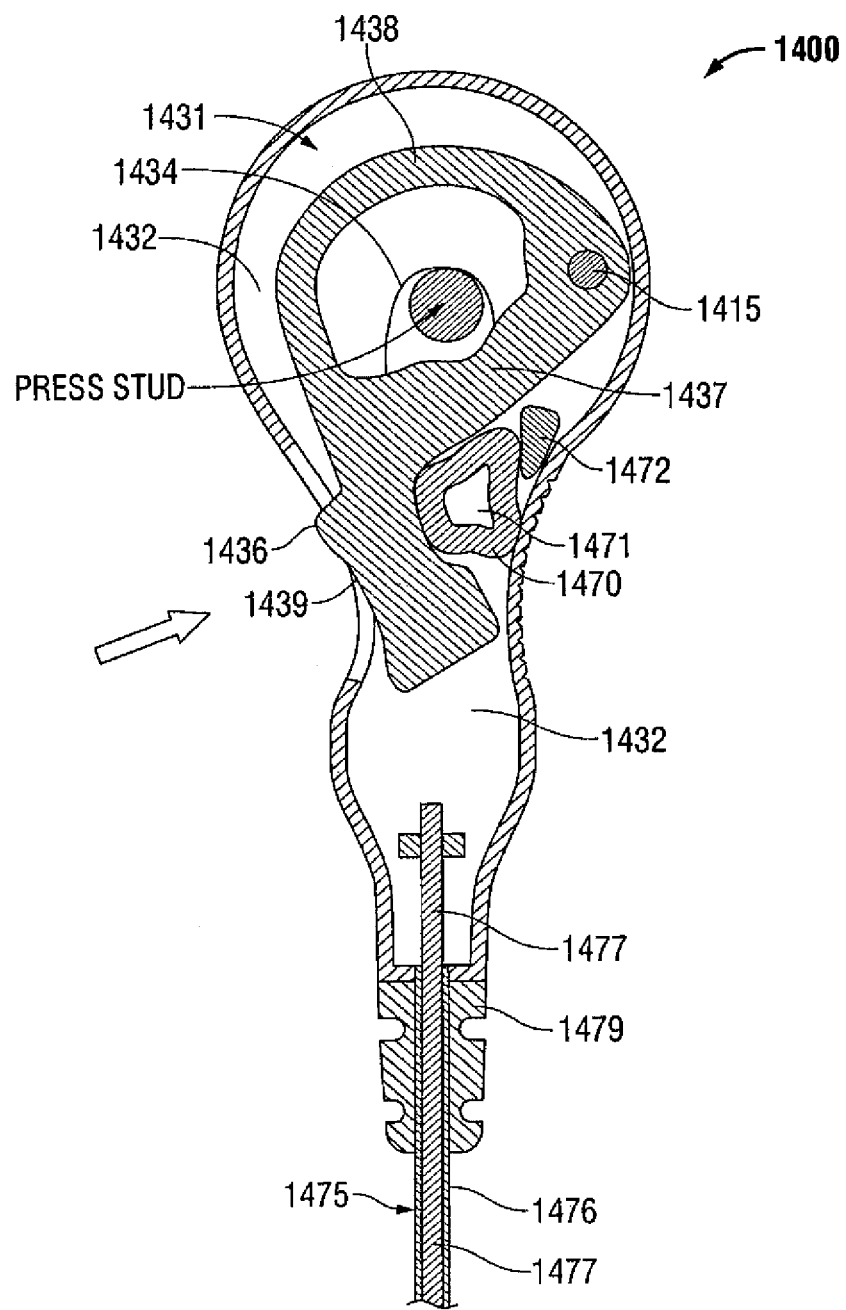
FIG. 3B is a view of the FIG. 3A embodiment in a disengaged configuration in accordance with the present disclosure.
Figure 3C:
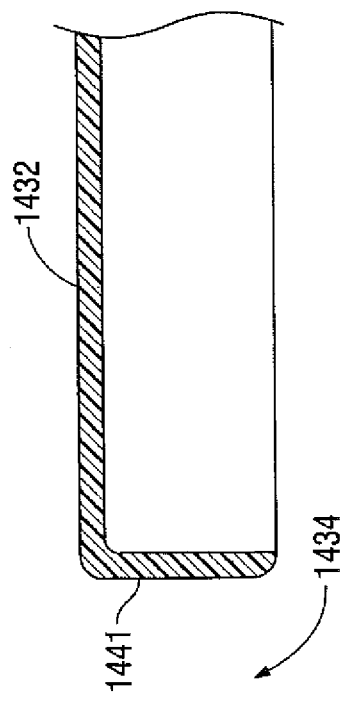
FIG. 3C is a detail view of a press stud opening of the FIG. 3A embodiment of a radiolucent ECG electrode connector in accordance with the present disclosure
Figure 3C:
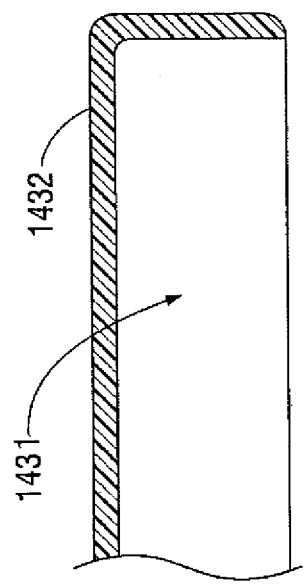

Accordingly, one aspect of the present invention provides an electrode connector which may be used during patient imaging. One embodiment of an ECG electrode connector of the present invention is shown in FIGS. 3A, 3B, and 3C. In view thereof, and so as not to obscure the present disclosure with redundant information, only those features distinct to ECG electrode connector 1400 will be described hereinafter.

ECG electrode connector 1400 is configured to facilitate the monitoring of ECG and other biological parameters while the subject patient is undergoing an imaging procedure, such as without limitation, MRI, CT, PET, and the like. Connector 1400 includes a housing 1424 having an interior recessed surface 1431 that includes an opening 1434 defined therein that opens to a patient-facing surface of the housing. Opening 1434 is dimensioned to accept the insertion of a head of a press stud of a patient electrode. Housing 1424 may be formed from any suitable non-conductive material, including polymeric material. The connector 1400 includes an engagement member 1436 having an actuation surface 1439, which may be a contoured pushbutton, and an engaging face 1437. Engagement member 1436 is pivotable about a pivot 1415 to enable the engaging face 1437 to move from a first position whereby engaging face 1437 is closer to a top portion 1425 of opening 1434 and a second position whereby engaging face 1437 is further from a top portion 1425 of opening 1434. By this arrangement, the bulbous head of a press stud that has been introduced into opening 1434 may be captured in opening 1434 between engaging face 1437 and a sidewall of opening 1434. Engagement member 1436 includes a stiffener 1438, that may have an arcuate shape, disposed between engaging face 1437 and pivot 1415.

The interior recessed surface 1431 of housing 1424 includes a radiolucent conductor 1432 that facilitates the conduction of biological signals between a press stud captured within opening 1434 and a lead wire conductor 1477.

Radiolucent conductor 1432 may be included with surface 1431 by any suitable manner, including without limitation, as a conductive coating and/or a conductive material incorporated within housing 1424 or associated portions thereof. In some embodiments, radiolucent conductor 1432 may be formed by dispersing conductive carbon powder over interior recessed surface 1431. The conductive carbon powder is then fused via the application of heat and/or pressure to the polymeric material that forms interior recessed surface 1431. In some embodiments, radiolucent conductor 1432 may be formed by the application of radiolucent conductive ink to interior recessed surface 1431. In other embodiments, the radiolucent conductor 1432 may comprise a carbon fiber wire fixed to the recessed surface 1431. As shown in FIG. 3C, radiolucent conductor 1432 may extend onto at least a portion of a sidewall 1441 of opening 1434.

ECG electrode connector 1400 includes a lead wire 1475 extending from a proximal (e.g., bottom) end thereof. Lead wire 1475 includes an outer insulator 1476 coaxially disposed about a conductor 1477. Conductor 1477 is formed from radiolucent electrically conductive material, such as conductive carbon or conductive carbon monofilament wire. In some embodiments, conductor 1477 is formed from one or more carbon fibers. A distal portion of the outer insulator is stripped thus exposing a distal portion of conductor 1477'. The exposed portion 1477' of conductor 1477 is operatively joined to radiolucent conductor 1432 of interior recessed surface 1431. Conductor 1477' may be joined by any suitable manner, including without limitation a crimping element 1478 and/or by radiolucent electrically conductive adhesive. In some embodiments, the exposed portion 1477' of conductor 1477 and radiolucent conductor 1432 are integrally formed. A strain relief 1479 surrounds a portion of lead wire 1475 where lead wire 1475 exits the housing 1424

A resilient member 1470 biases engagement member 1436 towards a first position whereby engaging face 1437 is closer to a top portion 1425 of opening 1434. Lobed resilient member 1470 is positioned between a recess 1428 defined in engagement member 1436 and a saddle 1472 provided by housing 1424. Resilient member 1470 may be formed from a radiolucent elastomer, including without limitation, silicone. Resilient member 1470 may have any shape to provide sufficient force to allow the desired movement of the engagement member 1436. The resilient member 1470 may have any regular or irregular shape, including circle, square, triangle, and clover. In one, one embodiment, resilient member 1470 is a lobed member. In the embodiment shown in FIGS. 3A and 3B, lobed resilient member 1470 includes a three-lobe profile having each lobe evenly spaced at about 120° apart, however, a lobed resilient member 1470 in accordance with the present disclosure may include fewer than three lobes, or more than three lobes. Additionally or alternatively, lobed resilient member 1470 may include lobes that are not evenly spaced and/or irregularly placed. The resilient member may be solid throughout, or comprise one or more openings. Lobed resilient member 1470 includes a center opening 1471 defined therein and having a shape that generally corresponds to the contour of the perimeter (e.g., the lobe profile) of lobed resilient member 1470, and/or that may include one or more interior projections 1481. The ratio of the size of opening 1471 to the overall size of the lobed resilient member 1470 determines, at least in part, the resiliency of lobed resilient member 1470 and may facilitate tactile feedback to a user during the actuation/compression and release/extension of the combination of lobed resilient member 1470 and engagement member 1436. For example, and without limitation, cooperative interference between one or more interior projections 1481 as resilient member 1470 is compressed and/or released may generate one or more vibrations that may, in turn, be sensed as tactile feedback by a user's fingertip via actuating surface 1439 and/or via housing 1424.

During use, a user may apply force to actuating surface 1439 using, e.g., a fingertip, thereby overcoming the biasing force of resilient member 1470 to cause engagement member 1436 to rotate slightly counterclockwise about pivot 1415. In turn, engaging face 1437 moves further from a top surface 1425 of opening 1434 which provides sufficient clearance to enable the introduction of a bulbous head of a press stud into opening 1434. Once the press stud is inserted into opening 1434, the user may remove finger pressure from actuating surface 1439, whereupon the biasing force of resilient member 1470 causes engagement member 1436 to rotate slightly clockwise about pivot 1415, thereby electromechanically engaging the press stud with a portion of opening 1434 and thus, electrically coupling the press stud with radiolucent conductor 1432 and conductor 1477.

Figure 4A:
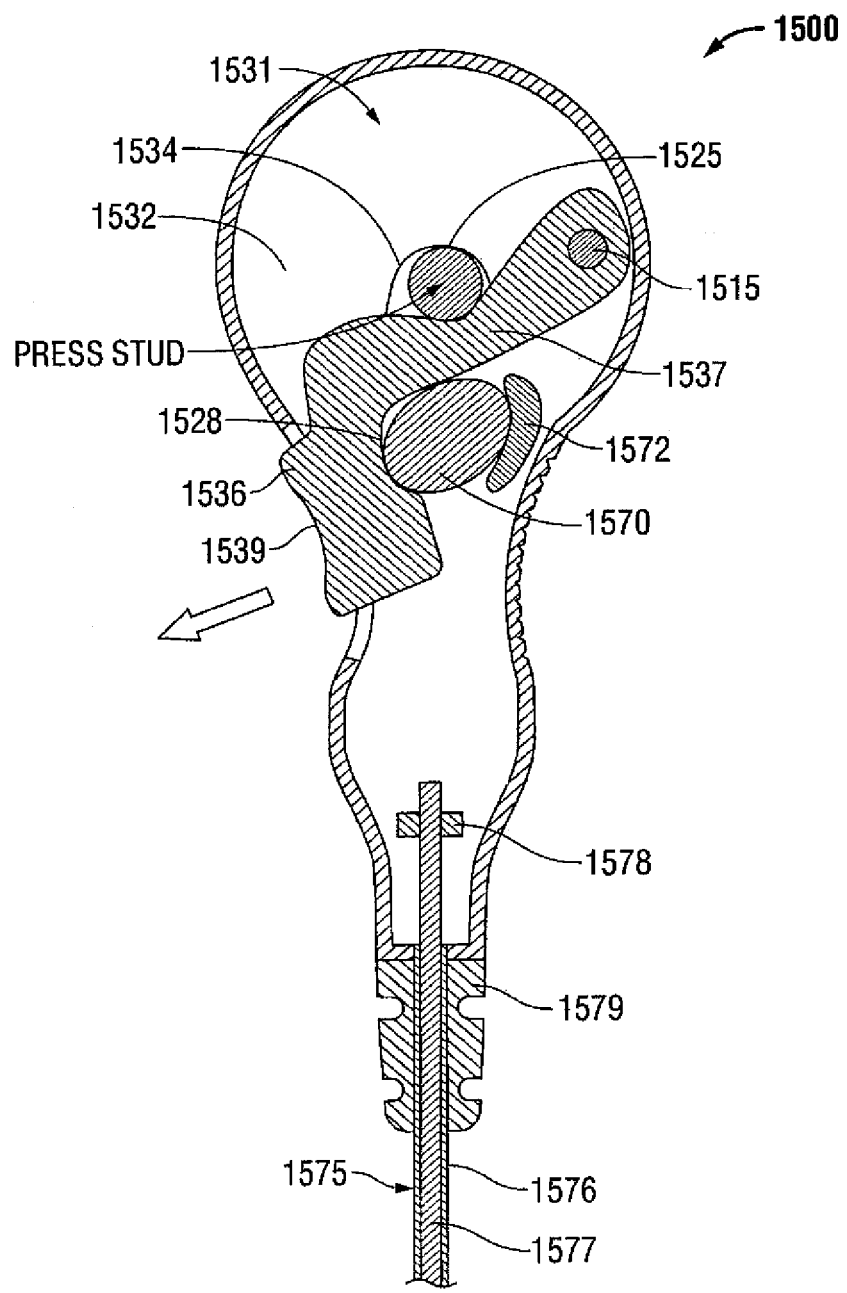
FIG. 4A is a view of another embodiment of a radiolucent ECG electrode connector in an engaged configuration in accordance with the present disclosure.
Figure 4B:
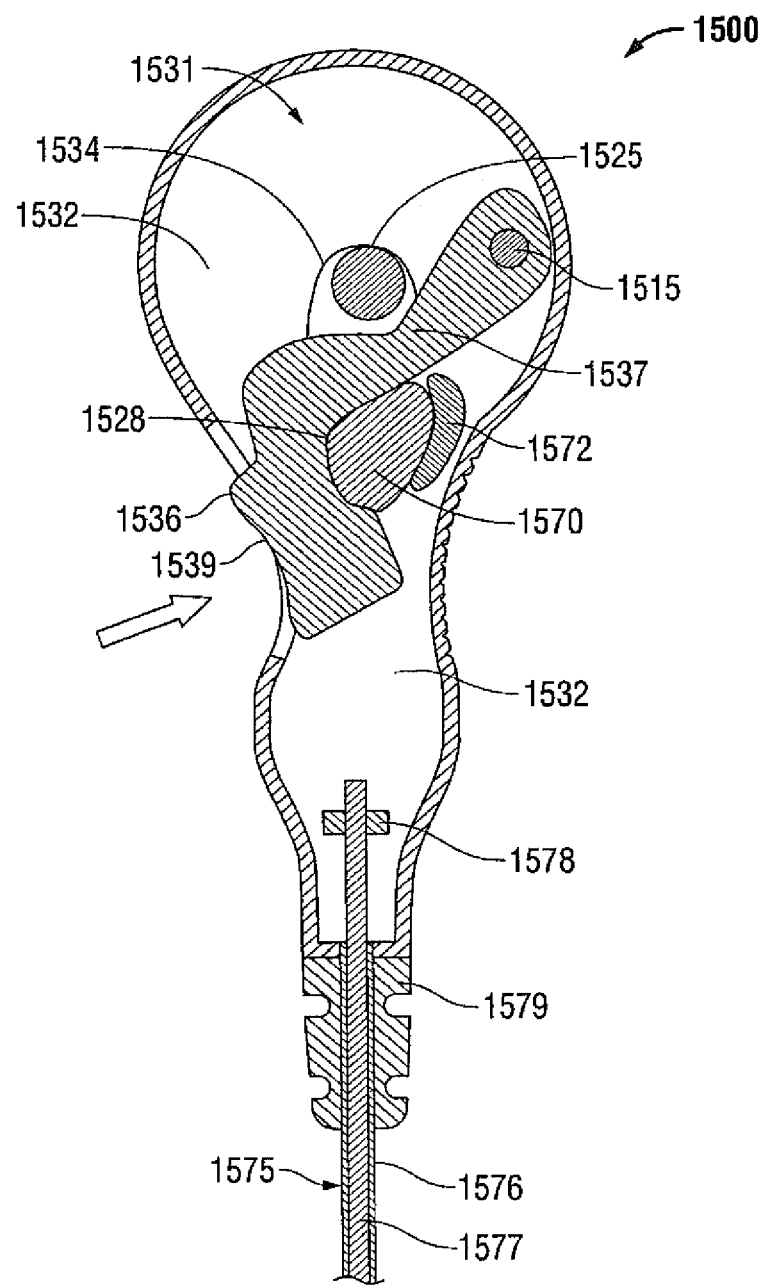
FIG. 4B is a view of the FIG. 4A embodiment in a disengaged configuration in accordance with the present disclosure.

Yet another embodiment of a radiolucent ECG electrode connector 1500 is shown in FIGS. 4A and 4B. In view thereof, and so as not to obscure the present disclosure with redundant information, only those features distinct to ECG electrode connector 1500 will be described hereinafter. Radiolucent electrode connector 1500 includes an engagement member 1536 having an actuation surface 1539, which may be a contoured pushbutton, and an engaging face 1537. Engagement member 1536 is pivotable about a pivot 1515 to enable the engaging face 1537 to move from a first position whereby engaging face 1537 is closer to a top portion 1525 of opening 1534 and a second position whereby engaging face 1537 is further from a top portion 1525 of opening 1534. By this arrangement, the bulbous head of a press stud that has been introduced into opening 1534 may be captured between engaging face 1537 and opening 1534.

A resilient member 1570 biases engagement member 1536 towards a first position whereby engaging face 1537 is closer to a top portion 1525 of opening 1534. Resilient member 1570 may have any shape to provide sufficient force to allow the desired movement of the engagement member 1536. The resilient member 1570 may have any regular or irregular shape, including circle, square, triangle, and clover, and may, but need not be solid throughout. In some embodiments resilient member 1570 has a generally spherical shape. Spherical resilient member 1570 is positioned between a recess 1528 defined in engagement member 1536 and a saddle 1572 provided by a housing 1524. Spherical resilient member 1570 may be formed from a radiolucent elastomer, including without limitation, silicone. In the embodiment shown in FIGS. 4A and 4B, spherical resilient member 1470 may include surface or internal features, such as without limitation, ribs, voids, and/or textures that may facilitate tactile feedback to a user during the actuation/compression and release/extension of the combination of spherical resilient member 1570 and engagement member 1536. In some embodiments resilient member 1570 may have a generally cylindrical shape, a generally ovoid shape, and/or or a compound shape that may include, e.g., a combination spherical, cylindrical, and/or ovoid shape. In some embodiments, resilient member 1570 may be hollow.

Figure 5:
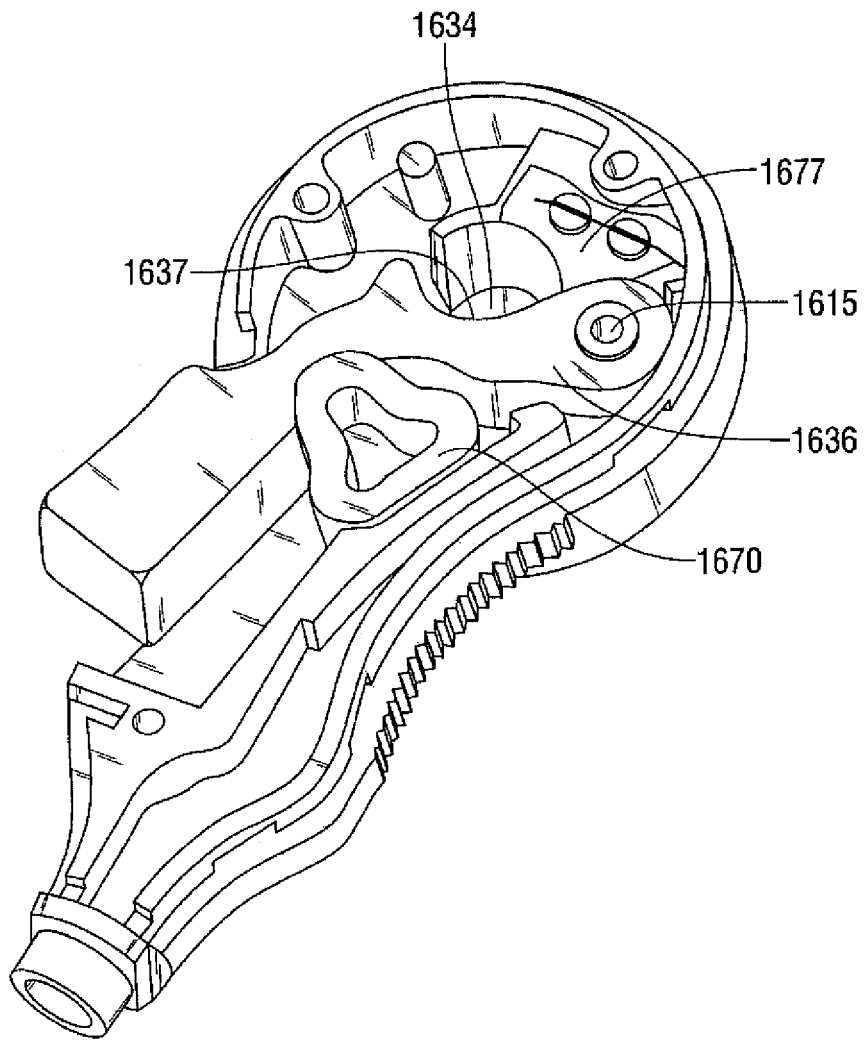
FIG. 5 is a view of another embodiment of a radiolucent ECG electrode connector in accordance with the present disclosure.

FIG. 5 shows in another embodiment of the present invention similar to the electrode connector shown in FIGS. 3A, 3B, and 3C. In view thereof, and so as not to obscure the present disclosure with redundant information, only those features distinct to ECG electrode connector 1600 will be described hereinafter. As seen in FIG. 5, opening 1634 which is dimensioned to accept the insertion of a head of a press stud of a patient electrode is bounded on at least one side by a conductor 1677. Conductor 1677 may have any size and shape as long as at least a portion of the conductor extend into opening 1634 along at least a portion of sidewall 1634. In one embodiment, conductor 1677 extends through opening 1634 to completely cover at least apportion of the circumference of the opening 1634. Conductor 1677 may be made of a radiolucent conductive material such as a conductive polymer or a conductive carbon. A radiolucent leadwire (not shown) formed of a conductive carbon may be positioned in a passageway 1699 of the connector housing and joined to conductor 1677. In use, once an electrode stud is positioned in opening 1634 and engagement member 1636 is released, engagement face 1637 captures the electrode stud between the engagement face 1637 and a portion of conductor 1677.

According to one aspect of the invention, the radiolucent electrode connectors of the present invention are advantageous because they need not be removed from a patient before imaging reducing the time required to administer often critical procedures. The radiolucent electrode connectors of the present invention may also increase patient safety by reducing or eliminating the dangers associated with imaging conventional electrode connectors. Moreover, the radiolucent electrode connectors of the present invention may allow ECG patient monitoring during imaging.

It will be understood that various modifications, alterations, and improvements will readily occur to those skilled in the art. Such modifications, alterations, and improvements are intended to be part of this disclosure, and are intended to be within the spirit and scope of the invention. Further variations of the above-disclosed and other features and functions, or alternatives thereof, may be desirably combined into many other different systems, instruments and applications. Various presently unforeseen or unanticipated alternatives, modifications, variations or improvements therein may be subsequently made by those skilled in the art, which are also intended to be encompassed by the following claims. Accordingly, the foregoing description and drawing are by way of example only.

What is claimed is:

1. An ECG connector assembly, comprising:
a housing having an interior recessed surface having disposed therein an opening dimensioned to operably receiving a press stud of an ECG electrode pad;
a radiolucent conductor disposed on at least a portion of the interior recessed surface; a radiolucent lead wire conductor extending from a proximal end of the housing and operably coupled to the radiolucent conductor;
an engagement member pivotably disposed upon the interior recessed surface and having an engaging face and a pivot, wherein the engagement member is pivotable between a first position whereby the engaging face is closer to a top portion of the opening and a second position whereby engaging face is further from a top portion of the opening;
an arcuate stiffener disposed between an end of the engaging face distal from the pivot and pivot of the engagement member; and
a radiolucent resilient member configured to bias the engagement member towards the first position;
wherein the arcuate stiffener is spaced apart from the engaging face.

2. The ECG connector assembly in accordance with claim 1, wherein the radiolucent resilient member includes a plurality of lobes.

3. The ECG connector assembly in accordance with claim 1, wherein the radiolucent resilient member includes a center opening defined therein.

4. The ECG connector assembly in accordance with claim 1, wherein the radiolucent resilient member includes one or more projections that cooperatively interfere to generate tactile feedback when the engagement member is moved between the first position and the second position.

5. The ECG connector assembly in accordance with claim 1, wherein the radiolucent conductor extends onto at least a portion of a sidewall of the opening.

6. The ECG connector assembly in accordance with claim 1, wherein the radiolucent conductor is formed from carbon.

7. The ECG connector assembly in accordance with claim 1, wherein
the radiolucent conductor is formed by:
dispersing conductive carbon powder over the interior recessed surface; and
fusing the conductive carbon powder to the interior recessed surface.

8. The ECG connector assembly in accordance with claim 1, wherein the radiolucent resilient member has a shape selected from the group consisting of substantially spherical, substantially cylindrical, or substantially ovoid.

9. The ECG connector assembly in accordance with claim 1, wherein the pivotable axis of the engagement member is orthogonal to the interior recessed surface.

* * * * *